(12) United States Patent
Winstrom (10) Patent No.: US 12,144,534 B2
(45) Date of Patent: Nov. 19, 2024

(54) SYSTEMS AND METHODS FOR MONITORING ELECTRODE TISSUE ENGAGEMENT DURING ABLATION

(71) Applicant: ADVANCED NEUROMODULATION SYSTEMS, INC., Plano, TX (US)

(72) Inventor: William Winstrom, Leander, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 937 days.

(21) Appl. No.: 16/446,458

(22) Filed: Jun. 19, 2019

(65) Prior Publication Data

US 2020/0323577 A1 Oct. 15, 2020

Related U.S. Application Data

(60) Provisional application No. 62/834,225, filed on Apr. 15, 2019.

(51) Int. Cl.
| | | |
|---|---|---|
| *A61B 18/16* | (2006.01) | |
| *A61B 18/12* | (2006.01) | |
| *A61B 18/14* | (2006.01) | |
| *A61B 18/00* | (2006.01) | |

(52) U.S. Cl.
CPC ...... *A61B 18/1233* (2013.01); *A61B 18/1492* (2013.01); *A61B 18/16* (2013.01); *A61B 2018/00577* (2013.01); *A61B 2018/1253* (2013.01)

(58) Field of Classification Search
CPC . A61B 18/1233; A61B 18/1492; A61B 18/16; A61B 2018/00577; A61B 2018/1253; A61B 2018/00898; A61B 18/1206; A61B 2018/00875; A61B 2018/1286; A61B 2090/065

See application file for complete search history.

(56) References Cited

U.S. PATENT DOCUMENTS

| | | | |
|---|---|---|---|
| 5,830,212 A | * | 11/1998 | Cartmell ............ A61B 18/1233 606/35 |
| 7,326,208 B2 | | 2/2008 | Vanney et al. |
| 2009/0171341 A1 | | 7/2009 | Pope et al. |
| 2009/0171345 A1 | | 7/2009 | Miller et al. |
| 2009/0198230 A1 | * | 8/2009 | Behnke .............. A61B 18/1233 606/35 |

(Continued)

*Primary Examiner* — Khadijeh A Vahdat
(74) *Attorney, Agent, or Firm* — Norton Rose Fulbright US LLP (57) ABSTRACT

An ablation system and method are provided. The ablation system includes an ablation power generator configured to generate ablation energy. An active electrode is coupled to the ablation power generator and is configured to deliver the ablation energy to ablation tissue of interest during an ablation procedure. A return electrode arrangement (REA) is coupled to the ablation power generator and is configured to engage remote tissue, at a remote location from the ablation tissue of interest, to provide a return path during the ablation procedure. The REA transitions between an engaged and disengaged state with the remote tissue. An electrode-tissue engagement (ETE) circuit includes a resonant circuit coupled to the REA. The ETE circuit is configured to detect when the REA is in the engaged state or disengaged state.

9 Claims, 5 Drawing Sheets

(56) References Cited

U.S. PATENT DOCUMENTS

| | | | |
|---|---|---|---|
| 2010/0217259 A1* | 8/2010 | Strauss | A61B 18/1233 606/38 |
| 2011/0190755 A1* | 8/2011 | Mathur | A61B 18/1233 606/33 |
| 2017/0135744 A1* | 5/2017 | Smith | A61B 18/1233 |

* cited by examiner

SYSTEMS AND METHODS FOR MONITORING ELECTRODE TISSUE ENGAGEMENT DURING ABLATION

CROSS REFERENCE TO RELATED APPLICATIONS

This application claims benefit to U.S. Provisional Application No. 62/834,225 filed Apr. 15, 2019, titled "Design of a Contact Quality Monitor (CQM) Circuit for use in an RF Ablation System", the subject matter of which is herein incorporated by reference in its entirety.

BACKGROUND

Embodiments herein generally relate to methods and systems for monitoring electrode tissue engagement during ablation.

Conventional ablation systems, such as radiofrequency (RF) ablation systems, may employ electrodes in a unipolar or monopolar mode to ablate tissue of interest. In monopolar ablation, ablation energy from an ablation power generator (e.g., an RF power generator) typically flows through an active electrode and into a tissue of interest. The ablation energy passes through the patient's body to return electrodes (or neutral electrodes or dispersive electrodes) where it is collected and returned to the ablation power generator. Return electrodes are typically implemented as dispersive pads.

In unipolar mode, only the active electrodes are placed at the ablation site. The active electrodes apply a high-frequency electrical current to tissue, resulting in therapeutic thermal effects (e.g., heating or cooling) proximate to the active electrode. The active electrodes are used to ablate, heat, cool, or modify tissue of interest. Return electrodes are placed at locations remote from the ablation site, typically on the skin of the patient, to complete an ablation circuit. Return electrodes are typically much larger than the active electrodes and, consequently, have a low current density.

The large area and low current density of the return electrodes mitigate against tissue heating and the risk of return electrode-induced patient burns provided that sufficient contact between the return electrodes and the patient's skin is maintained. However, sometimes the return electrodes may partially detach, reducing the contact area and increasing the current density at the return electrode site. The reduced contact area may cause excessive heating to an extent that the patient's underlying tissue is burned. The present IEC 60601-2-2 standard requires that no acceptable neutral electrode should exceed a 6 Celsius temperature rise when subjected to a select current and duration test. For acceptable performance and operation, the return electrodes should have sufficient contact and operate within the present IEC standard, or related standards. Accordingly, it is desirable to provide an ablation system capable of monitoring whether or not sufficient contact exists between the return electrodes and the patient.

SUMMARY

In accordance with embodiments herein, an ablation system is provided. The ablation system includes an ablation power generator configured to generate ablation energy. An active electrode is coupled to the ablation power generator and is configured to deliver the ablation energy to ablation tissue of interest during an ablation procedure.

A return electrode arrangement (REA) is coupled to the ablation power generator and is configured to engage remote tissue, at a remote location from the ablation tissue of interest, to provide a return path during the ablation procedure. The REA transitions between an engaged and disengaged state with the remote tissue. An electrode-tissue engagement (ETE) circuit includes a resonant circuit coupled to the REA. The ETE circuit is configured to detect when the REA is in the engaged state or disengaged state.

Optionally, the ETE circuit may generate an engagement state signal that may vary based on an impedance level between first and second return electrodes within the REA. The ETE circuit may further comprise a closed loop oscillator connected to a primary side of the transformer. The closed loop oscillator may have an oscillation frequency corresponding to a resonant frequency of the resonant circuit. The closed loop oscillator may generate the engagement state signal. The ETE circuit may further comprise a filter, amplifier and rectifier configured to process the engagement state signal to form a processed state signal. The ETE circuit may further comprise a level detector configured to generate an error signal indicating when the REA is in the engaged state or disengaged state based on the processed state signal. The resonant circuit may further comprise a transformer having a secondary side connected across first and second return electrodes in the REA and a capacitor bank connected across the first and second return electrodes, the capacitor bank and transformer forming the resonant circuit.

Optionally, the transformer and capacitor bank may define an inductance and a capacitance of the resonant circuit. The ablation system may include a closed loop oscillator connected to a primary side of the transformer. The closed loop oscillator may comprise an amplifier network connected to a current limiting feedback resistor. The amplifier network may be configured to generate a signal based on a resonant frequency of the resonant circuit. The system may further comprise a level detector configured to output an indicator of when the REA is in the engaged state or disengaged state based on the signal from the amplifier network.

Optionally, the capacitor bank may further comprise first and second capacitors connected in series between the first and second return electrodes. The first and second capacitors may be connected to one another at an intermediate ground node. The transformer may further comprise first and second windings on the secondary side connected across the first and second capacitors, respectively. The first and second windings may be connected to one another at the intermediate ground node. The REA may comprise two return electrodes. The REA may comprise a plurality of return electrodes. The ablation system may comprise one or more processors and a memory coupled to the one or more processors. The memory may store specific executable instructions. The instructions may be executable by the one or more processors to test and select a return electrode pair of a plurality of return electrodes within the REA based on the indicator generated by the level detector.

In accordance with embodiments herein, a method is provided. The method includes contacting a patient with a return electrode arrangement (REA) coupled to an ablation power generator. The REA engages a remote tissue, at a remote location from ablation tissue of interest, to provide a return path during an ablation procedure. The REA transitions between an engaged state and a disengaged state with the remote tissue. The method delivers ablation energy to the ablation tissue of interest at an active electrode coupled to the ablation power generator and detects, at an electrode-tissue engagement (ETE) circuit that includes a resonant circuit coupled to the REA, when the REA is in the engaged state or disengaged state.

Optionally, the method may generate, at the ETE circuit, an engagement state signal that may vary based on an impedance level between first and second return electrodes within the REA. The REA may further comprise a closed loop oscillator connected to a primary side of a transformer. The closed loop oscillator may have an oscillation frequency corresponding to a resonant frequency of the resonant circuit. The method may generate, at the closed loop oscillator, the engagement state signal. The ETE circuit may further comprise a filter, amplifier and rectifier. The method may process, at the ETE, the engagement state signal to form a processed state signal. The ETE circuit may comprise a level detector. The method may generate, at the level detector, an error signal indicating when the return electrode is in the engaged state or disengaged state based on the processed state signal.

Optionally, the resonant circuit may be connected to a secondary side of a transformer and a closed loop oscillator may be connected to a primary side of the transformer. The closed loop oscillator may comprise an amplifier network. The method may generate, at the amplifier network, a signal based on a resonant frequency of the resonant circuit. The system may comprise a level detector. The method may output, at the level detector, an indicator of when the REA is in the engaged state or the disengaged state based on the signal from the amplifier network. The method, under control of one or more processors of the ablation system configured with specific executable instructions, may stop ablation when the level detector indicates a disengaged state. The method, under control of one or more processors of the ablation system configured with specific executable instructions, may generate an alert when the level detector indicates a disengaged state. The method, under control of one or more processors of the ablation system configured with specific executable instructions, may test and select a return electrode pair of a plurality of return electrodes within the REA based on the indicator generated by the level detector.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. in other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Terms

The terms "engaged state" and "attached state" shall mean a condition in which the return electrode arrangement (REA) contacts and is conductively seated against tissue (e.g., skin surface) in a manner that avoids an undesirable temperature rise at the tissue (e.g., skin surface) proximate to the REA. It is recognized that, when in an engaged state, a surface area of the electrodes in the REA may be entirely in contact with tissue. Additionally, when in an engaged state, a small portion of the surface area of the electrodes in the REA may not contact the tissue (e.g., less than 25% of the surface area of one or more electrodes in the REA).

The terms "disengaged state" and "detached state" shall mean a condition in which the REA is at least partially disconnected in a non-conductive arrangement with the tissue (e.g., skin surface). In the disengaged state, the electrodes of the REA may be entirely, or only partly, separated from the tissue, where the extent of separation is sufficient to give rise to an undesirable temperature rise, at the tissue proximate to the REA. By way of example, the REA may be considered to be in a disengaged state when more than 25% of the surface area of one or more electrodes in the REA are not properly seated against tissue. As another example, the REA may be considered to be in a disengaged state, independent of the surface area of the electrodes seated against tissue, but instead based on an extent to which the tissue at the REA experiences heating or a temperature rise. For example, when the nature of the engagement between the REA and the tissue causes the tissue to rise in temperature by a predetermined amount (e.g., more than 5° or 10°), the REA may be considered to be in a disengaged state. For example, a nature of the engagement that gives rise to temperature change may be when the REA moves or shifts causing intermittent engagement. As another example, a nature of the engagement that gives rise to temperature change may be when the REA is not firmly pressed against the tissue.

The term "ablation" shall refer generally to procedures for ablating, heating, or modifying a tissue of interest using ablation energy.

The terms "connector" and "connection", as used herein, represent or refer to one or more electrical nodes and do not imply a particular type of physical interface mechanism.

Overview

Figure 1:
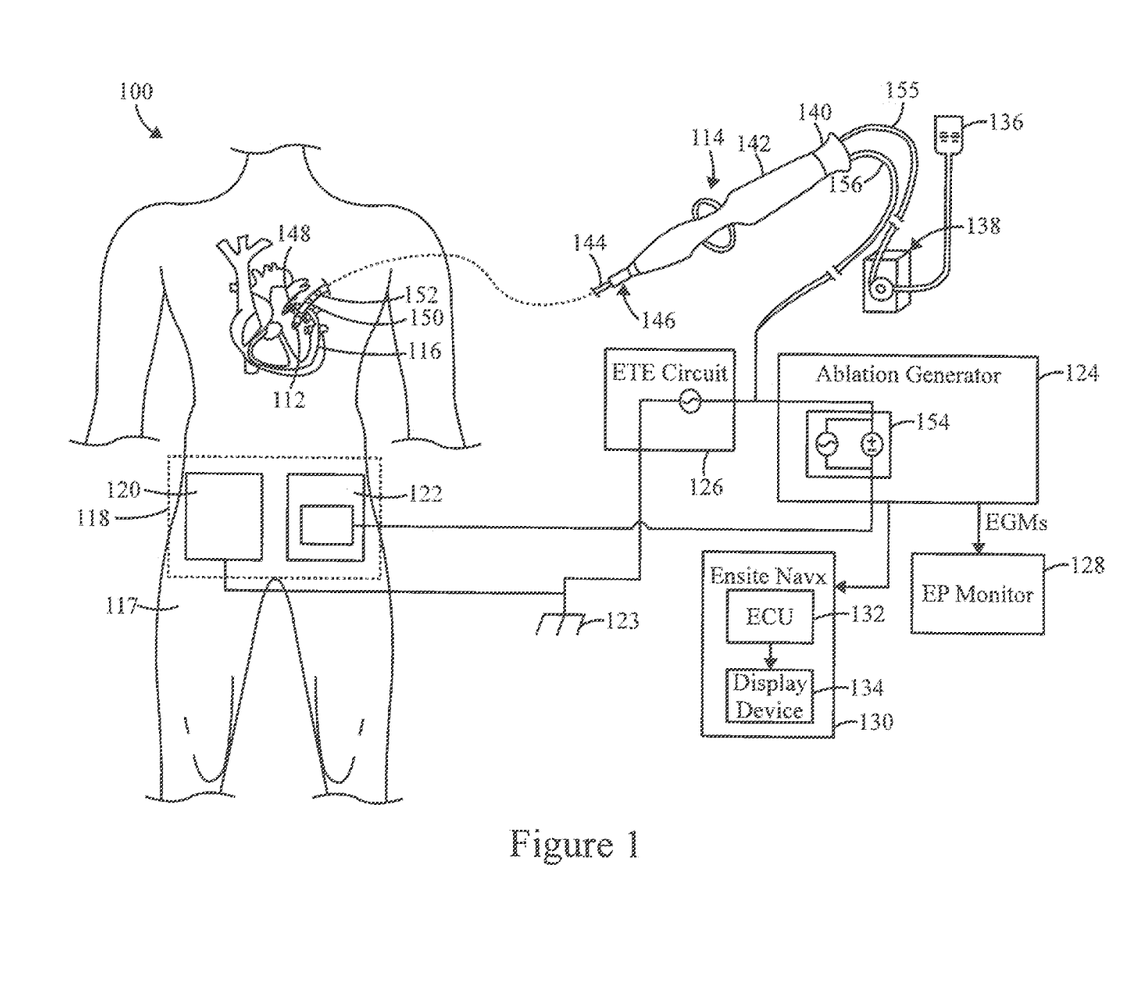
FIG. 1 is a diagrammatic view of an example of an ablation system in accordance with embodiments herein.

FIG. 1 illustrates one example of an ablation system 100 for providing one or more diagnostic and therapeutic functions in accordance with embodiments herein. The ablation system 100 includes an active electrode 112 on a catheter 114 for ablating an ablation tissue of interest 116 in a patient's body. The active electrode 112 on the catheter 114 is coupled to an ablation power generator 124. The ablation system 100 further includes a return electrode arrangement or REA 118 coupled to the ablation power generator 124. In the illustrated embodiment, the ablation tissue of interest 116 comprises heart or cardiac tissue. It should be understood, however, that the present embodiments may be used to monitor the REA 118 regardless of the location of the ablation tissue of interest 116. The active electrode 112 of catheter 114 may be any type of electrode useful in delivering ablation energy to an ablation tissue of interest, for example, intracardiac electrodes, needle electrodes, patch electrodes, wet brush electrodes (such as the electrodes disclosed in commonly assigned U.S. patent application Ser. No. 11/190,724 filed Jul. 27, 2005, the entire disclosure of which is incorporated herein by reference), virtual electrodes (e.g., those formed from a conductive fluid medium such as saline including those disclosed in commonly assigned U.S. Pat. No. 7,326,208 issued Feb. 5, 2008, the entire disclosure of which is incorporated herein by reference), and the like. Optionally, the ablation system 100 may further include an electrophysiology (EP) monitor 128 and a system 130 for visualization, mapping and navigation of internal body structures. The system 130 may include an electronic control unit 132 and a display device 134 among other components.

The catheter 114 is provided for examination, diagnosis and treatment of internal body tissues such as ablation tissue of interest 116. In accordance with one embodiment of the invention, the catheter 114 comprises an ablation catheter and, optionally, an irrigated RF ablation catheter. It should be understood, however, that aspects herein may be implemented and practiced regardless of the type of ablator (e.g., catheter, wand, knife, loop, etc.) The catheter 114 may be connected to a fluid source 136 having a biocompatible fluid such as saline through a pump 138 (which may comprise, for example and without limitation, a fixed rate roller pump or variable volume syringe pump with a gravity feed supply from fluid source 136 as shown) for irrigation. The catheter 114 is also electrically connected to ablation power generator 124 for delivery of ablation energy (e.g., RF energy). The catheter 114 may include a cable connector or interface 140, a handle 142, a shaft 144 having a proximal end 146 and a distal end 148 and one or more electrodes 112, 150, 152. The catheter 114 may also include other conventional components not illustrated herein such as a temperature sensor, additional electrodes, and corresponding conductors or leads.

The connector 140 provides mechanical, fluid and electrical connection(s) for cables 155, 156 extending from pump 138 and the ablation power generator 124. The connector 140 may be disposed at the proximal end 146 of the catheter 114.

The handle 142 provides a location for the clinician to hold the catheter 114 and may further provide means for steering or guiding the catheter shaft 144 within the patient's body. For example, the handle 142 may include means to change the length of a guidewire extending through the catheter 114 to the distal end 148 of the shaft 144 to steer the shaft 144. The construction of handle 142 may vary depending on the characteristics of the catheter 114.

The shaft 144 is an elongated, tubular, flexible member configured for movement within the patient's body. The shaft 144 supports active electrode 112, ring electrodes 150, 152, and their associated conductors, and optionally additional electronics used for signal processing or conditioning. The shaft 144 may also provide for transport, delivery and/or removal of fluids (including irrigation fluids and bodily fluids), medicines, and/or surgical tools or instruments. The shaft 144 may be formed from conventional materials such as polyurethane and may define one or more lumens configured to house and/or transport electrical conductors, fluids or surgical tools. The shaft 144 may be introduced into a blood vessel or other structure within a patient's body through a conventional introducer. The shaft 144 may be steered or guided through the patient's body to a desired location such as ablation tissue of interest 116 with guide wires or the like.

The electrodes 112, 150, 152 may be provided for a variety of diagnostic and therapeutic purposes including, for example, ablation, electrophysiological studies, catheter identification and location, pacing, cardiac mapping, and the like. In one example, the catheter 114 may include an active electrode 112 (e.g., an ablation tip electrode) at the distal end 148 of the shaft 144 and a pair of ring electrodes 150, 152. It should be understood, however, that the number, orientation and purpose of the electrodes 112, 150, 152 may vary.

The REA 118 functions as a return path for the ablation energy applied at the active electrode 112 during an ablation procedure and is configured to engage remote tissue, at a location remote from the ablation tissue of interest. The REA 118 includes at least return electrodes 120, 122 and, optionally, additional electrodes. The return electrodes 120, 122 may be connected to one another at an intermediate ground node 123. The REA 118 may also serve additional purposes such as providing RF or navigational signal injection paths, sensing electrical potentials, facilitating the generation of an electromechanical map, and the like. The return electrodes 120, 122 may include a flexible, electrically conductive material and are configured for affixation to a patient's tissue (e.g., in electrical contact with a surface of the patient's skin 117). In one example, the return electrodes 120, 122 may be spaced relatively far apart. In the illustrated embodiment, return electrodes 120, 122 are, respectively, located on the medial aspects of the right lea and the left leg. Additionally, or alternatively, the return electrodes 120, 122, may be located on the front and back of the torso, at different locations on the back of the torso, or in other orientations.

The ablation power generator 124 generates, delivers and controls ablation energy (e.g., RF energy) used by the catheter 114. The ablation power generator 124 may be, for example, the commercially available unit sold under the model number 1500T9-CP RF Cardiac Ablation Generator, available from Abbott Laboratories or the like. The ablation power generator 124 may include an ablation signal source 154 (e.g., an RF ablation signal source) configured to generate an ablation signal that is output across a pair of source connectors; a positive polarity connector SOURCE (+) which may connect to active electrode 112, and a negative polarity connector SOURCE (−) which may be electrically connected by conductors or lead wires to one or more of return electrodes 120, 122 within the REA 118 or intermediate ground node 123. The ablation signal source 154 may be configured to generate a signal at a predetermined frequency in accordance with one or more user specified parameters (e.g., power, time, etc.) and under the control of one or more processors configured with program instructions and other feedback sensing and control circuitry. The ablation signal source 154 may generate a signal, for example, with a frequency of 450 kHz or greater. The ablation power generator 124 may also monitor various parameters associated with the ablation procedure including impedance, the temperature at the distal end 148 of the catheter 114, ablation energy and the position of the catheter 114 and provide feedback to the clinician regarding these parameters.

System for Monitoring Electrode Tissue Engagement

In accordance with embodiments herein, methods and systems implement an electrode-tissue engagement (ETE) circuit, within an ablation system 100, for monitoring electrode-tissue engagement during an ablation procedure. The ETE circuit monitors the state of the REA 118 in order to reduce or eliminate return electrode-induced patient burns during an ablation procedure. If the return electrodes 120, 122 within the REA 118 maintain an engaged state during an ablation procedure, the REA is conductively seated against the patient's tissue (e.g., skin surface) in a manner and to an extent that avoids an undesirable temperature rise at the tissue proximate to the REA 118. However, portions of, or the entirety of, one or more return electrodes 120, 122 within the REA 118 may detach from the patient's tissue during an ablation procedure in a manner, and to an extent, that an undesirable temperature rise at the tissue proximate to the REA 118 occurs, giving rise to a risk of injury in a disengaged state of the REA 118. Alternatively, the return electrodes 120, 122 within the REA 118 may remain partially conductively seated against the patient's tissue but still cause an undesirable temperature rise at the tissue proximate to the REA 118, giving rise to a disengaged state of the REA 118. Accordingly, monitoring the state of the REA 118 includes detecting when the REA 118 is in an engaged state or a disengaged state.

The ETE circuit 126 generates and processes an engagement state signal that varies based on an impedance level between return electrode 120 and return electrode 122. The impedance level between return electrodes 120, 122 will vary based on the portion of the surface area of the electrodes in conductive contact with the patient's tissue (e.g., skin surface). Based on the impedance level, the ETE circuit 126 generates an error signal indicating whether the REA 118 is in the engaged state or the disengaged state as described further below. In one example, when the impedance level between the return electrodes 120, 122 falls within 2000Ω±50Ω in the presence of ablation and a circuit induced current of less than 100 μA AC RMS or 10 μA DC, the ETE circuit 126 generates an error signal indicating that the REA 118 is in the engaged state. Alternatively, when the impedance level between the return electrodes 120, 122 falls outside of 2000Ω±50Ω in the presence of ablation and a circuit induced current of less than 100 μA AC RMS or 10 μA DC, the ETE circuit 126 generates an error signal indicating that the REA 118 is in the disengaged state.

Optionally, the REA 118 can include three or more electrodes and the ablation system 100 can employ a switching system to select electrode pairs from the three or more electrodes. Thus, the one or more processors of the ablation system may successively test combinations of return electrode pairs to select a return electrode pair in an engaged state.

Figure 2:
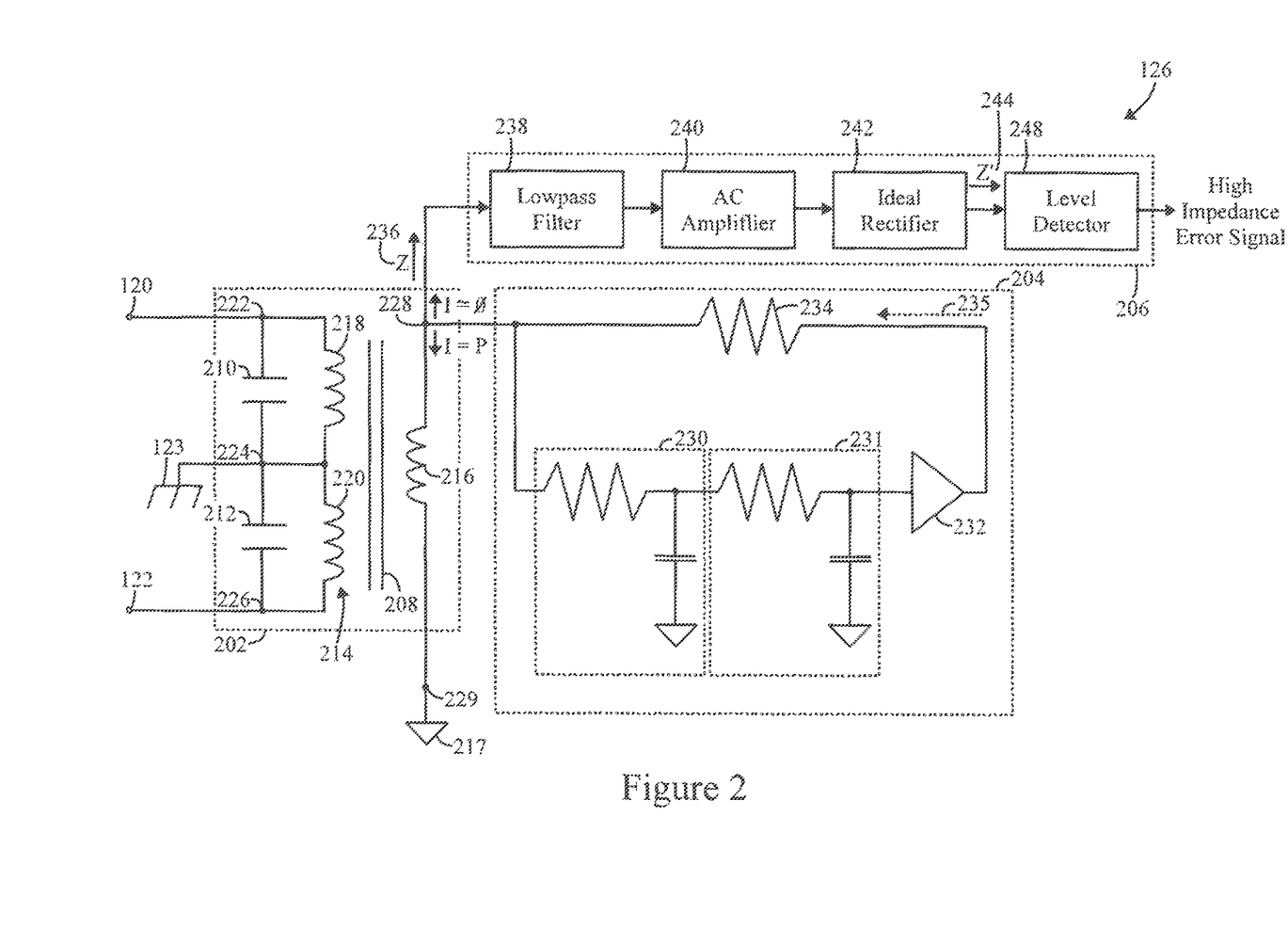
FIG. 2 illustrates a block diagram of an example of an ETE circuit in accordance with embodiments herein.

FIG. 2 illustrates an example block diagram of an ETE circuit 126 formed in accordance with embodiments herein. The ETE circuit 126 includes a resonant circuit 202 connected to a closed loop oscillator 204 and a detection circuit 206 as described further below.

The resonant circuit 202 includes a transformer 208 connected in parallel with first and second capacitors 210, 212. The transformer 208 has a transformer primary 216 and a transformer secondary 214. The transformer secondary 214 includes first, second and third taps 222, 224, 226. The transformer secondary 214 includes a first winding 218 between the first and second taps 222, 224 thereof and a second winding 220 between the second and third taps 224, 226 thereof. The first and second taps 222, 224 are connected across opposing sides of the first capacitor 210, while the second and third taps 224, 226 are connected across opposing sides of the second capacitor 212. The return electrodes 120, 122 are connected, respectively, in series to the first and third taps 222, 226 of the transformer secondary 214. The intermediate ground node 123 is connected in series to the tap 224 of the transformer secondary 214. The capacitors 210, 212 form a capacitor bank connected in series across the return electrodes 120, 122 within the REA 118 and are connected to each other at an intermediate ground node 123, thereby shunting the output of the transformer 208. The transformer 208 and the capacitor bank (e.g., the capacitors 210, 212) define an inductance and a capacitance of the resonant circuit 202. The resonant frequency of the resonant circuit 202 varies based on variation of an impedance level, across the opposing taps 222, 226 of the transformer secondary 214, between the return electrodes 120, 122 within the REA 118.

The transformer primary 216 of the resonant circuit 202 includes the taps 228 and 229 positioned on opposing sides thereof. The transformer primary 216 is connected in series to a circuit return 217 at the tap 229 and is connected in series to the closed loop oscillator 204 at the tap 228. The closed loop oscillator 204 includes an amplifier network (or other equivalent circuit) having a current-limiting feedback resistor 234 implemented on its feedback side (as represented by dashed arrow 235). The closed loop oscillator 204 has an oscillation frequency that corresponds to the resonant frequency of the resonant circuit 202. The amplifier network, in addition to feedback resistor 234, includes at least a first resistive-capacitive (RC) bank 230 and a second RC bank 231 implemented in series between and connecting the tap 228 of the transformer primary 216 and the input of the amplifier 232 to modify the phase of the engagement state signal (Z) 236 creating the phase shift necessary for it to oscillate at the resonant frequency of the resonant circuit 202. The output of the amplifier 232 is connected in series to the current-limiting feedback resistor 234. The current-limiting feedback resistor 234 is connected to the tap 228 of the transformer primary 216, completing the loop. Each of the at least first and second RC banks 230, 231 includes a resistor connected to a first side of a capacitor and a circuit return connected to the second side of the capacitor. The current in the transformer secondary 214 of the transformer 208 (e.g., the current flowing in the patient) is controlled by the electrical properties (e.g., resistance, impedance, or the like) of the feedback resistor 234. The feedback resistor 234 may be selected, based on the output swing of the amplifier 232, to have a sufficient impedance to limit the circuit-induced current on the transformer secondary 214, from the circuit-induced current applied across the transformer primary 216 from the tap 228 (as indicated by $I_p$), of the transformer 208 to be less than a select value (e.g., 100 µA AC RMS, 10 µA DC, or the like). Additionally, the closed loop oscillator 204 generates an engagement state signal (Z) 236 that varies based on the resonant frequency of the resonant circuit 202. The engagement state signal (Z) 236 changes from an engaged to a disengaged state based on the impedance level between the return electrodes 120, 122 of the REA 118. The engagement state signal (Z) 236, upon resonance of the resonant circuit 202, is the reflected impedance of the return electrodes 120, 122. The engagement state signal (Z) 236 is represented as a voltage value due to the resonant state of the resonant circuit 202 and is indicated by the negligible current (I=0) flowing upwards from the tap 228. Accordingly, the oscillation frequency of the closed loop oscillator 204 may be controlled to be much lower than the frequency of the ablation signals produced by the ablation power generator 124 to facilitate signal processing of the engagement state signal (Z) 236 by the detection circuit 206. For example, the resonant circuit 202 may resonate at frequencies of 1-2 kHz causing the closed loop oscillator 204 to generate an engagement state signal (Z) 236 having osculation frequencies of 1-2 kHz, while the ablation power generator 124 outputs ablation signals having a frequency of 450 kHz or greater. Furthermore, the engagement state signal 236, corresponding to the resonant frequency of the resonant circuit 202, varies based on the impedance level between the return electrodes 120, 122 within the REA 118. In another example, the closed loop oscillator 204 may be implemented as a low fixed frequency oscillator to drive the transformer 208 and generate the engagement state signal (Z) 236.

The transformer primary 216 is also connected in series to the detection circuit 206 at the tap 228. The engagement state signal (Z) 236 at the transformer primary 216 of the transformer 208 is processed by the detection circuit 206. The detection circuit 206 includes a filter 238 (e.g., a low-pass filter), an amplifier 240 (e.g., an AC amplifier), a rectifier 242 (e.g., an ideal rectifier), and a level detector 248, connected in serial in that order. The filter 238 receives the engagement state signal (Z) 236 (e.g., as a voltage value) and attenuates ablation frequency signals produced by the ablation power generator 124. For example, the filter 238 is a low-pass filter having a cutoff frequency of 4 kHz, that passes a 1-2 kHz engagement state signal from the closed loop oscillator 204 but attenuates ablation frequency signals having much higher frequencies (e.g., 450 kHz or greater). Additionally, or alternatively, the filter 238 is a low-pass filter having a cut-off frequency that is 50% higher than the value of the oscillation frequency of the closed loop oscillator 204. The low pass filter 238 passes the engagement state signal (Z) 236 to the AC amplifier. The AC amplifier 240 amplifies the engagement state signal (Z) 236 and passes the engagement state signal (Z) 236 to the ideal rectifier 242. The ideal rectifier 242 rectifies the engagement state signal 236. The filter 238, the amplifier 240, and the rectifier 242 serially process the engagement state signal (Z) 236 to output a processed state signal (Z) 244 to the level detector 248. The level detector 248 receives the processed state signal (Z') 244 and generates an error signal indicating when the REA 118 is in the engaged state or disengaged state based whether the value of the processed state signal (Z') 244 falls within or outside threshold values (e.g., above or below a threshold value) over a select time. The threshold value may be selected such that there is a lag between the processed state signal (Z) 244 exceeding (or falling below) the threshold value and the patient incurring return electrode-induced burns. For example, when the processed state signal (Z') 244 corresponds to the impedance level between the return electrodes 120, 122 within the REA 118 falling within 200Ω±50Ω, the error signal indicates that the REA 118 is in an engaged state. Alternatively, when the processed state signal (Z') 244 corresponds to the impedance level between the return electrodes 120, 122 within the REA 118 falling outside of 200Ω±50Ω, the error signal indicates that the REA 118 is in a disengaged state.

Figure 3:
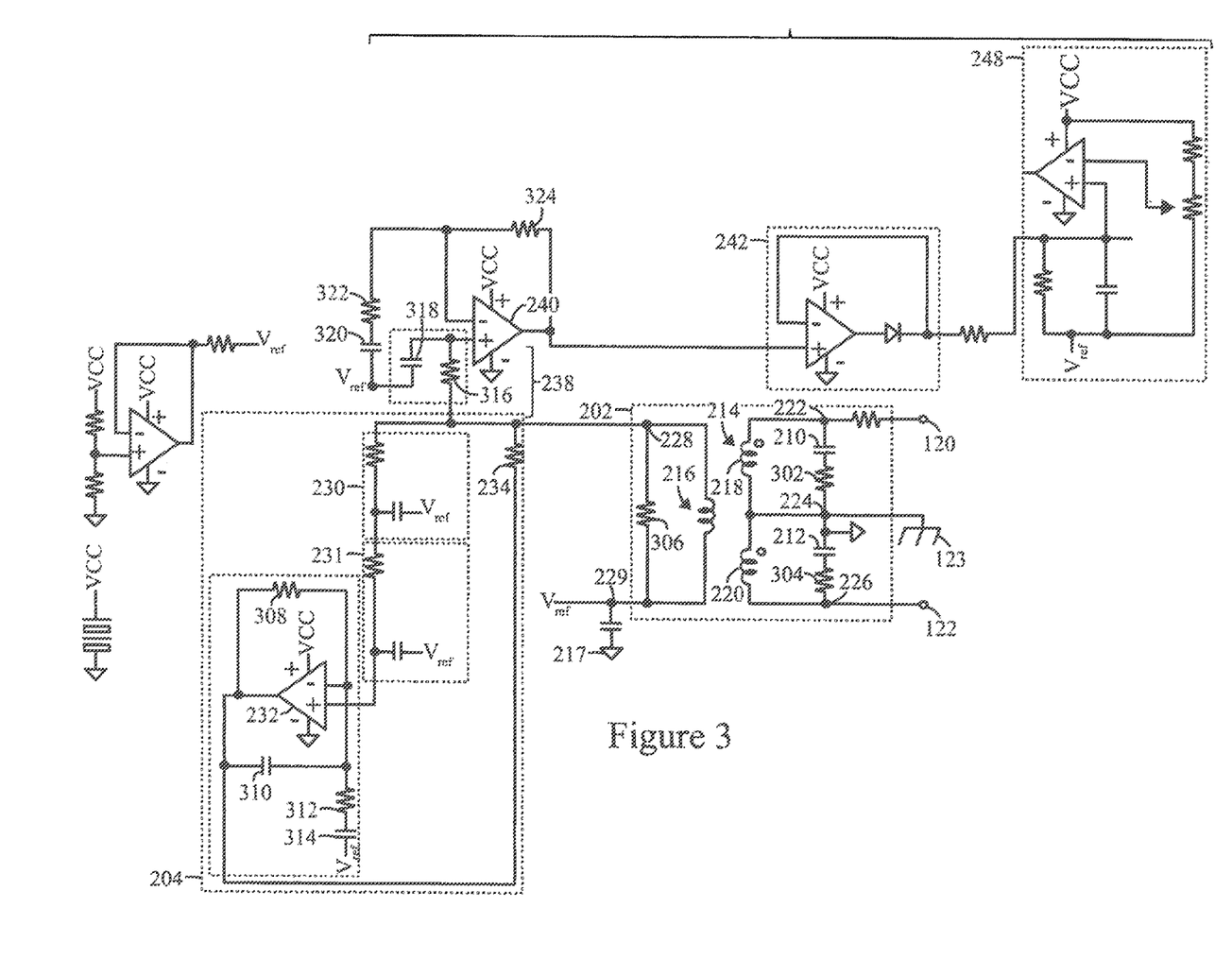
FIG. 3 illustrates a circuit diagram of one example of an ETE circuit of FIG. 2 in accordance with embodiments herein.

FIG. 3 illustrates a circuit diagram of one example of an ETE circuit 126 of FIG. 2 in accordance with embodiments herein. The resonant circuit 202 includes the transformer 208 connected in parallel with the first and second capacitors 210, 212, hi one example, the transformer 208 is a Murata 77203C transformer. The transformer 208 includes the transformer primary 216 and the transformer secondary 214. The transformer secondary 214 includes the first, second and third taps 222, 224, 226. The transformer secondary 214 includes the first winding 218 between the first and second taps 222, 224 thereof and the second winding 220 between the second and third taps 224, 226 thereof. The first and second taps 222, 224 are connected across opposing sides of the first capacitor 210, while the second and third taps 224, 226 are connected across opposing sides of the second capacitor 212. The return electrodes 120, 122 are connected, respectively, in series to the first and third taps 222, 226 of the transformer secondary 214. The intermediate ground node 123 is connected in series to the tap 224 of the transformer secondary 214. The capacitors 210, 212 form the capacitor bank connected in series across the return electrodes 120, 122 within the REA 118 and are connected to each other at an intermediate ground node 123, thereby shunting the output of the transformer 208. The resistors 302, 304 in series with the capacitors 210, 212, respectively, represent energy loss due to the parasitic effects of the capacitors 210, 212. The transformer 208 and the capacitor bank (e.g., the capacitors 210, 212) define the inductance and the capacitance of the resonant circuit 202. The resonant frequency of the resonant circuit 202 varies based on variation of the impedance level, across the opposing taps 222, 226 of the transformer secondary 214, between the return electrodes 120, 122 within the REA 118.

The transformer primary 216 of the resonant circuit 202 includes the taps 228 and 229 positioned on opposing sides thereof. The transformer primary 216 is connected in series to the circuit return 217 at the tap 229 and is connected in series to the closed loop oscillator 204 at the tap 228. The resistor 306 in parallel with the transformer primary 216 and connected across the taps 228, 229 represents energy loss of the transformer 208 due to the winding of the transformer primary 216, the windings 218, 220 of the transformer secondary 214, and an inductive core (not shown) positioned within the windings. The closed loop oscillator 204 includes the amplifier network (or other equivalent circuit) having the current-limiting feedback resistor 234. The closed loop oscillator 204 is tuned to have an oscillation frequency that corresponds to the resonant frequency of the resonant circuit 202. In one example, the amplifier network, in addition to the feedback resistor 234, includes at least the first RC bank 230 and the second RC bank 231 implemented in series between and connecting the tap 228 of the transformer primary 216 and the positive terminal of amplifier 232. Each of the at least first and second RC banks 230, 231 include the resistor connected to a first side of the capacitor and the circuit return connected to the second side of the capacitor. The RC banks 230, 231 modify the phase of the engagement state signal (Z) 236 generated by the closed bop oscillator 204. The resistor 308 and capacitor 310 connected in parallel with and across the input terminals and the output terminal of the amplifier 232, as well as the resistor 312 and capacitor 314 connected in series with the inputs of the resistor 308, the capacitor 310, the input terminals of the amplifier 232, and the reference voltage wet, cooperate to limit the voltage swing of the amplifier 232 to a select value. The select value of the voltage swing of the amplifier 232 sets the gain of the amplifier 232 so that it can oscillate at the resonant frequency of the resonant circuit 202. In one example, the select value of the voltage swing of the amplifier 232 is ±3.3V. The output of the amplifier 232 is connected in series to the current-limiting feedback resistor 234. In one example, the value of the current-limiting feedback resistor 234 is 2.4 kΩ. The current-limiting feedback resistor 234 is connected to the tap 228 of the transformer primary 216, completing the loop. The current in the transformer secondary 214 of the transformer 208 (e.g., the current flowing in the patient) is controlled by the value of the feedback resistor 234. The feedback resistor 234 may be selected, based on the output swing of the amplifier 232, to have a sufficient impedance to limit the circuit-induced current on the transformer secondary 214, from the circuit-induced current applied across the transformer primary 216 from the tap 228 (as indicated by $I_p$ in FIG. 2), of the transformer 208 to be less than a select value (e.g., 100 μA AC RMS, 10 μA DC, or the like). The engagement state signal (Z) 236 (shown in FIG. 2), corresponds to the resonant frequency of the resonant circuit 202 and varies based on the impedance level between the return electrodes 120, 122 within the REA 118.

The transformer primary 216 is also connected in series to the detection circuit 206 at the tap 228. The engagement state signal (Z) 236 output by the closed loop oscillator 204 at the transformer primary 216 is processed by the detection circuit 206. The detection circuit 206 includes the filter 238 (e.g., a low-pass filter), the amplifier 240 (e.g., an AC amplifier), the rectifier 242 (e.g., an ideal rectifier), and the level detector 248, connected in serial in that order. The filter 238 receives the engagement state signal (Z) 236 (e.g., as a voltage value) and attenuates ablation frequency signals produced by the ablation power generator 124. The filter 238 includes a resistor 316 and a capacitor 318 connected in series between the tap 228 and the input terminals of the AC amplifier 240. The low pass filter 238 passes the engagement state signal (Z) 236 to the AC amplifier. The capacitor 320, the resistor 322, the resistor 324, and the reference voltage $v_{ref}$, connected across the input and output terminals of the AC amplifier 240 cooperate to limit the voltage swing of the AC amplifier 240 to a select value. The AC amplifier 240 amplifies the engagement state signal (Z) 236 and passes the engagement state signal (Z) 236 to the ideal rectifier 242. The ideal rectifier 242 rectifies the engagement state signal 236. For example, the ideal rectifier 242 is a peak rectifier that outputs peak voltage. The filter 238, the amplifier 240, and the rectifier 242 serially process the engagement state signal (Z) 236 to output a processed state signal (Z') 244 (shown in FIG. 2) to the level detector 248. The level detector 248 receives the processed state signal (Z') 244 and, based thereon, generates an error signal indicating when the REA 118 is in the engaged state or disengaged state based whether the value of the processed state signal (Z') 244 falls within or outside threshold values (e.g., above or below a threshold value) over a select time. In one example, the level detector 248 is adjustable to facilitate calibration of the threshold value(s) on prior to an ablation procedure.

Additionally, the ETE circuit 126 may be stable over all operational states of the ablation system 100. During an ablation procedure, the ablation power generator 124 generates power at varied levels. For example, the ETE circuit 126 may have an equivalent resistance (measured in Ohms) of 200Ω when the ablation power generator 124 is operated at maximum power (e.g., 50 W) and an equivalent resistance of 185Ω when the ablation power generator 124 is not in operation. As such, the ETE circuit 126 may experience only up to a 15Ω increase in equivalent resistance when the ablation power generator 124 is activated. Thus, variation in the equivalent resistance of the ETE circuit 126 based on the operational state of the ablation power generator 124 is unlikely to result in false detection of the state of the REA 118. Additionally, or alternatively, any effects of the operational state of the ablation power generator 124 on the equivalent resistance of the ETE circuit 126 may be calibrated out, as well.

Method for Monitoring Electrode Tissue Engagement

Figure 4:
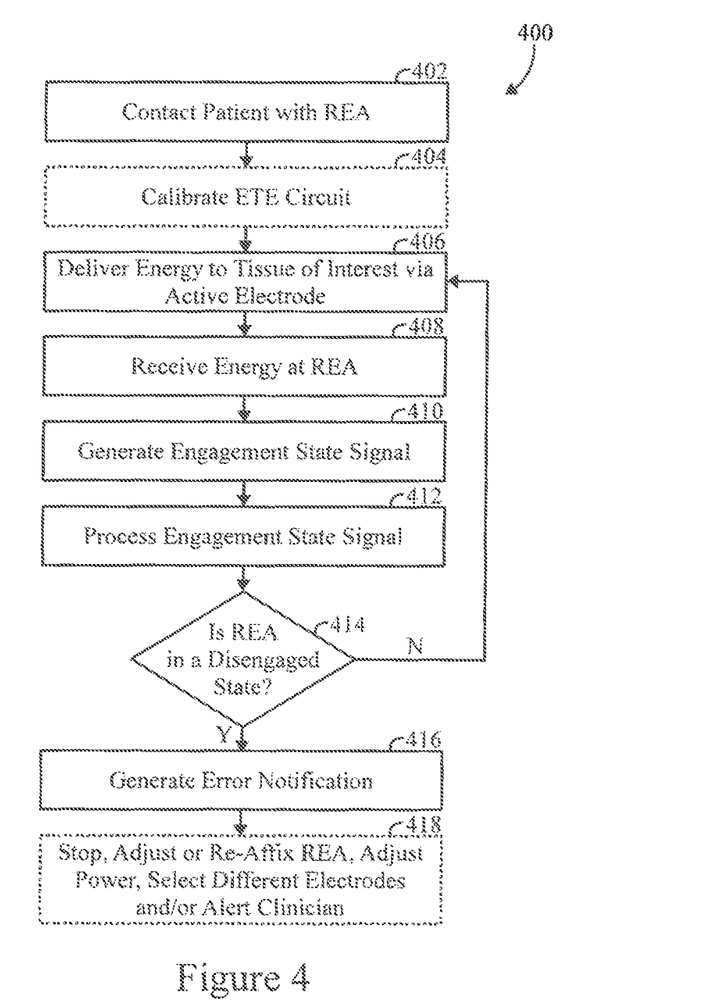
FIG. 4 illustrates a flow block diagram of a method of monitoring electrode tissue engagement in accordance with embodiments herein.

FIG. 4 illustrates a method 400 for monitoring electrode tissue engagement. Monitoring electrode tissue engagement includes monitoring the state of the REA in order to reduce or eliminate return-electrode induced burns during an ablation procedure. In one example, the method 400 is performed utilizing the systems and methods described in detail in relation to FIGS. 1-3. A portion of the operations of FIG. 4 may be implemented by one or more processors of the ablation system 100 configured with executable instructions. It should be recognized that while the operations of method 400 are described in a somewhat serial manner, one or more of the operations of method 400 may be continuous and/or performed in parallel with one another. For example, the various operations of the ablation system 100 may be continuous and/or performed in parallel with one another and/or other functions of the ablation system.

Beginning at 402, return electrodes 120, 122 within the REA 118 are applied to a remote tissue (e.g., the surface of the patient's skin 117) in an engaged state. The remote tissue may be at a remote location from the ablation tissue of interest 116. Ideally, the return electrodes 120, 122 are applied to the remote tissue such that all or nearly all of each return electrode 120, 122 is conductively seated against the remote tissue to an extent and in a manner that the REA 118 is initially in an engaged state. The REA 118 may optionally include additional electrodes. The return electrodes 120, 122 establish a return path for ablation energy to the ablation power generator 124. The return electrodes 120, 122 are also connected, respectively, to the opposing taps 222, 226 of the transformer secondary 214. The resonant frequency of the resonant circuit 202 varies based on variation of the impedance level, across the opposing taps 222, 226 of the transformer secondary 214, between the return electrodes 120, 122 within the REA 118. (Optional operation 404 is a calibration operation described further below.)

At 406, one or more processors of the ablation system direct the ablation power generator 124 to deliver ablation energy via the active electrode 112 to the ablation tissue of interest 116.

At 408, ablation energy delivered to the ablation tissue of interest 116 is received at the REA 118. The REA 118 provides a return path to the ablation power generator 124 for the ablation energy originally applied to the ablation tissue of interest 116 during an ablation procedure. The return electrodes 120, 122 within the REA 118 are also connected in series to the first and third taps 222, 226, respectively, of the transformer secondary 214. The capacitors 210, 212 form a capacitor bank connected in series across the return electrodes 120, 122 within the REA 118 and are connected to each other at an intermediate ground node 123, thereby shunting the output of the transformer 208. The transformer 208 and the capacitor bank (e.g., the capacitors 210, 212) define an inductance and a capacitance of the resonant circuit 202. The resonant frequency of the resonant circuit 202 varies based on variation of an impedance level, across the opposing taps 222, 226 of the transformer secondary 214, between the return electrodes 120, 122 within the REA 118. In one example, the resonant circuit 202 resonates at frequencies of 1-2 kHz based on the state of the REA 118. In an additional or alternative example, the return electrodes 120, 122 of the REA 118 have a circuit-induced current of less than a select value upon receipt of ablation energy during an ablation procedure. The current in the transformer secondary 214 of the transformer 208 (e.g., the current flowing in the patient) is controlled by the electrical properties (e.g., resistance, impedance, or the like) of the feedback resistor 234 implemented in the closed loop oscillator 204. For example, the feedback resistor 234 is selected, based on the output swing (e.g., ±3.3V) of the amplifier 232 of the closed loop oscillator 204, to have a sufficient impedance (e.g., 2.4 kΩ) to limit the circuit-induced current on the transformer secondary 214, from the circuit-induced current applied across the transformer primary 216 from the tap 228 (as indicated by $I_p$), of the transformer 208 to be less than a select value (e.g., 100 µA AC RMS, 10 µA DC, or the like).

At 410, the ETE circuit 126 generates, at the closed loop oscillator 204, an engagement state signal (Z) 236 that varies based on the resonant frequency of the resonant circuit 202. The closed loop oscillator 204 is connected to the transformer primary 216 at the tap 229. The closed loop oscillator 204 includes an amplifier network (or other equivalent circuit) having a current-limiting feedback resistor 234 implemented therein. The closed loop oscillator 204 has an oscillation frequency that corresponds to the resonant frequency of the resonant circuit 202. The amplifier network, in addition to feedback resistor 234, includes a plurality of RC banks 230, 231 implemented in series between and connecting the tap 228 of the transformer primary 216 and the input of the amplifier 232 to modify the phase of the engagement state signal (Z) 236 creating the phase shift necessary for it to oscillate at the resonant frequency of the resonant circuit 202. The output of the amplifier 232 is connected in series to the current-limiting feedback resistor 234. The current-limiting feedback resistor 234 is connected to the tap 228 of the transformer primary 216, completing the bop. The engagement state signal (Z) 236 generated by the closed loop oscillator 204 is represented as a voltage value due to the negligible current (I≈0) flowing upwards from the tap 228. Also, the oscillation frequency of the closed loop oscillator 204 may be controlled to be much lower than the frequency of the ablation signals produced by the ablation power generator 124 in order to facilitate signal processing of the engagement state signal (Z) 236 by the detection circuit 206. For example, the closed loop oscillator 204 is tuned to generate an engagement state signal (Z) 236 having oscillation frequencies of 1-2 kHz for a corresponding resonant circuit that resonates at 1-2 kHz, while the ablation power generator 124 outputs ablation signals having a frequency of 450 kHz or greater. Furthermore, the engagement state signal 236, corresponding to the resonant frequency of the resonant circuit 202, varies based on the impedance level between the return electrodes 120, 122 within the REA 118. In another example, the closed loop oscillator 204 may be implemented as a low fixed frequency oscillator to drive the transformer 208 and generate the engagement state signal (Z) 236.

At 412, the ETE circuit 126 processes, at the filter 238, the amplifier 240, and the rectifier 242 of the detection circuit 206, the engagement state signal (Z) 236. The detection circuit 206 includes a filter 238 (e.g., a low-pass filter), an amplifier 240 (e.g., an AC amplifier), a rectifier 242 (e.g., an ideal rectifier), and a level detector 248, connected in serial in that order. The filter 238 receives the engagement state signal (Z) 236 (e.g., as a voltage value) and attenuates ablation frequency signals produced by the ablation power generator 124. For example, the filter 238 is a low-pass filter having a cutoff frequency of 4 kHz, that passes a 1-2 kHz engagement state signal from the closed loop oscillator 204 but attenuates ablation frequency signals having much higher frequencies (e.g., 450 kHz or greater). Additionally, or alternatively, the filter 238 is a low-pass filter having a cut-off frequency that is 50% higher than the value of the oscillation frequency of the closed loop oscillator 204. The low pass filter 238 passes the engagement state signal (Z) 236 to the AC amplifier. The AC amplifier 240 amplifies the engagement state signal (Z) 236 and passes the engagement state signal (Z) 236 to the ideal rectifier 242. The ideal rectifier 242 rectifies the engagement state signal 236. The filter 238, the amplifier 240, and the rectifier 242 serially process the engagement state signal (Z) 236 to output a processed state signal (Z') 244 to the level detector 248.

At 414, the ETE circuit 126 generates, at a level detector 248 of the detection circuit 206, an error signal indicating when the REA 118 is in the engaged state or disengaged state. The level detector 248 receives the processed state signal (Z) 244 and generates an error signal indicating when the REA 118 is in the engaged state or disengaged state based whether the value of the processed state signal (Z) 244 falls within or outside threshold values (e.g., above or below a threshold value) over a select time. The threshold value may be selected such that there is a lag between the processed state signal (Z') 244 exceeding (or failing below) the threshold value and the patient incurring return electrode-induced burns. For example, when the processed state signal (Z') 244 corresponds to the impedance level between the return electrodes 120, 122 within the REA 118 falling within 200Ω±50Ω, the error signal indicates that the REA 118 is in an engaged state. Alternatively, when the processed state signal (Z') 244 corresponds to the impedance level between the return electrodes 120, 122 within the REA 118 falling outside of 200Ω±50Ω, the error signal indicates that the REA 118 is in a disengaged state. If the level detector 248 detects that the processed state signal represents an engaged state of the REA 118, the error signal indicates that the REA 118 is in the engaged state. In the engaged state, the REA 118 contacts the patient's tissue (e.g., the surface of the patient's skin 117) in a manner and to an extent that avoids an undesirable temperature rise at the tissue proximate to the REA 118. If the error signal indicates that the REA 118 is in the engaged state, flow returns to 406, and the process repeats. Alternatively, if the level detector 248 detects that the processed state signal represents a disengaged state of the REA 118, the error signal indicates that the REA 118 is in the disengaged state. In the disengaged state, the REA 118 is separated from the patient's tissue (e.g., the surface of the patient's skin 117) in a manner and to an extent that gives rise to an undesirable temperature rise at the patient's tissue proximate to the REA 118. If the error signal indicates that the REA 118 is in the disengaged state, flow moves to 416.

At 416, the ETE circuit 126 generates an error notification. The error notification is transmitted to the one or more processors of the ablation system 100 and/or to a clinician.

Figure 5:
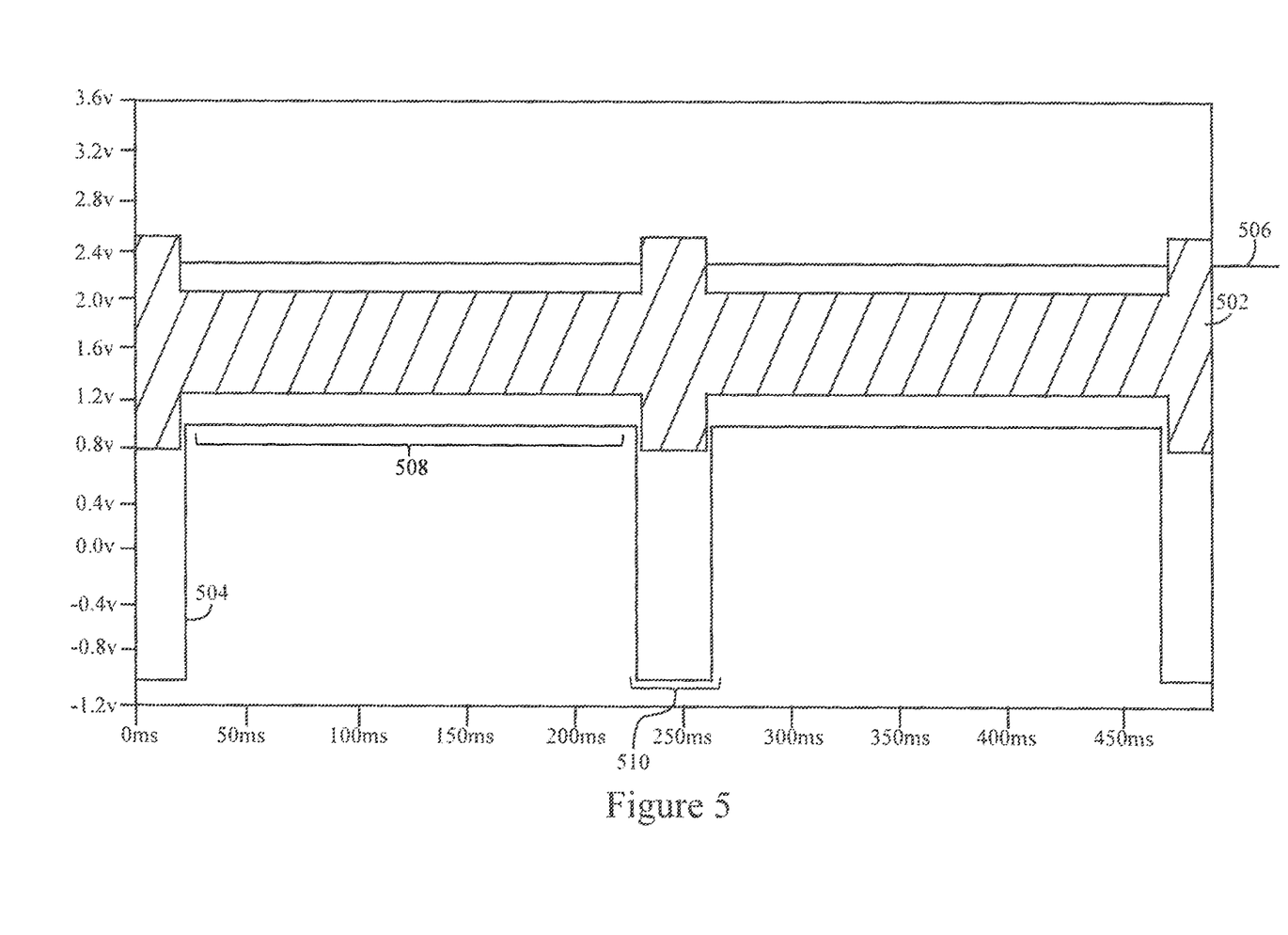
FIG. 5 illustrates an example of an engagement state signal in accordance with embodiments herein.

FIG. 5 illustrates an example of a processed state signal 502 based on the resonant circuit 202 having a resonant frequency of 1.9 kHz. The horizontal axis represents time and the vertical axis represents voltage. Graph 504 corresponds to the impedance value between the return electrodes 120, 122 at the REA over time. Graph 506 corresponds to a threshold value of voltage below which the REA 118 is in an engaged state and above which the REA 118 is in a disengaged state. At time 508, the impedance value between the return electrodes 120, 122 corresponds to an impedance value of the REA 118 in an engaged state. The processed state signal 502 at time 508 falls below the threshold indicated by graph 506. At time 510, the impedance value between the return electrodes 120, 122 corresponds to an impedance value of the REA 118 in a disengaged state. The processed state signal 502 at time 510 exceeds the threshold indicated by graph 506.

With respect to the operations of FIG. 4, the return electrodes 120, 122 of the REA 118 receive ablation energy originally applied to the ablation tissue of interest 116 at operation 408. The return electrodes 120, 122 are connected to opposing sides of the secondary &de 214 of transformer 208 and to each other via capacitors 210, 212. The resonant circuit 202 formed by transformer 208 and capacitors 210, 212 has a resonant frequency that corresponds to the impedance level between the return electrodes 120, 122 of the REA 118. At 410, the closed loop oscillator 204 generates an engagement state signal (z) 236 that corresponds to the resonant frequency of the resonant circuit 202. The engagement state signal (Z) 236 is processed at operation 412 to a processed state signal (Z') 244. At 414, the level detector 248 detects whether the processed state signal exceeds or falls below a threshold (indicated by graph 506). At time 508, the processed state signal 502 fails below the threshold (indicated by graph 506) of the level detector 248. When the processed state signal 502 falls below the threshold, the level detector 248 generates an error signal indicating the REA 118 is in an engaged state and the process continues. At time 510, the processed state signal 502 exceeds the threshold (indicated by graph 506) of the level detector 248. When the processed state signal 502 exceeds the threshold, the level detector 248 generates an error signal indicating the REA 118 is in a disengaged state and the ETE circuit 126 generates an error notification at operation 416.

Optionally, at 418, based on the error notification, the one or more processors of the ablation system 100 directs the ablation power generator 124 to cease delivering ablation energy, to adjust the power supplied via the active electrode 112 to the ablation tissue of interest 116 and/or select a different pair of return electrodes of the REA 11$ that are in an engaged state. Additionally, or alternatively, the one or more processors of the ablation system 100 provides an alert to the clinician communicating that the REA 118 is in a disengaged state and the patient is at risk of return electrode-induced burn. Additionally, or alternatively, the one or more processors of the ablation system 100 provides an alert to the clinician indicating that adjustment and/or re-affixation of the return electrodes 120, 122 of the REA 118 is needed to avoid a risk of return-electrode induced burn.

Optionally, at 404 and after the REA electrodes have been applied in a known engaged state at operation 402, the ETE circuit 126 of the ablation system 100 is calibrated for the patient. A calibration operation includes determining the impedance level of the return electrodes 120, 122 of the REA 118 for a patient based on a known engaged state of the REA 118. Determining the impedance level of the return electrodes 120, 122 of the REA 118 based on a known engaged state of the REA 118 includes applying ablation energy to an ablation tissue of interest 116 in a calibration mode to determine the processed state signal (Z') 244 output at the ideal rectifier 242 of the detection circuit 206 corresponding to the REA 118 in the engaged state according to operations 406-412. Based on the value(s) of the processed state signal (Z) 244 for the REA 118 in the engaged state, a threshold value of the level detector 248 is confirmed or adjusted.

Closing

It may be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "controller circuit," "circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only and are thus not intended to limit in any way the definition and/or meaning of the term "controller circuit".

The computer, subsystem, controller circuit, and/or circuit execute a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, subsystem, controller circuit, and/or circuit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable and include any computer program stored in memory for execution by a computer, including RAM memory, ROM memory, EPROM memory, EEPROM memory, and non-volatile RAM (NVRAM) memory. The above memory types are exemplary only and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc, are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A method, comprising:
   contacting a patient with a return electrode arrangement (REA) coupled to an ablation power generator, the REA engaging a remote tissue, at a remote location from ablation tissue of interest, to provide a return path during an ablation procedure, wherein the REA transitions between an engaged state and a disengaged state with the remote tissue;
   delivering ablation energy to the ablation tissue of interest at an active electrode coupled to the ablation power generator; and
   detecting, at an electrode-tissue engagement (ETE) circuit that includes a resonant circuit coupled to the REA and a closed loop oscillator, when the REA is in the engaged state or disengaged state based on the ablation energy received by the REA, and where the ETE circuit is configured to:
      generate an engagement state signal via the closed loop oscillator, wherein the engagement state signal varies based on an impedance level between first and second return electrodes within the REA;
      receive, at a filter of the ETE circuit, a composite signal that includes an output of the resonant circuit and the engagement state signal; and
      filter, by the filter, the output of the resonant circuit from the composite signal to extract the engagement state signal, and wherein the REA is detected to be in the engaged state or the disengaged state based on the engagement state signal.

2. The method of claim 1, wherein the closed loop oscillator is connected to a primary side of a transformer, the closed loop oscillator having an oscillation frequency corresponding to a resonant frequency of the resonant circuit.

3. The method of claim 2, wherein the ETE circuit further comprises an amplifier and a rectifier; the method further comprising:
   processing, at the ETE, the engagement state signal via the amplifier and rectifier to form a processed state signal.

4. The method of claim 3, wherein the ETE circuit further comprises a level detector; the method further comprising:
   generating, at the level detector, an error signal indicating when the return electrode is in the engaged state or disengaged state based on the processed engagement state signal.

5. The method of claim 1, wherein the resonant circuit is connected to a secondary side of a transformer and a closed loop oscillator is connected to a primary side of the transformer, the closed loop oscillator comprising an amplifier network; the method further comprising:
   generating, at the amplifier network, the engagement state signal based on a resonant frequency of the resonant circuit.

6. The method of claim 5, wherein the method further comprises a level detector, the method further comprising:
   outputting, at the level detector, an indicator of when the REA is in the engaged state or the disengaged state based on the engagement state signal from the amplifier network.

7. The method of claim 6, further comprising, under control of one or more processors of the ablation power generator configured with specific executable instructions, stopping ablation when the level detector indicates the REA is in the disengaged state.

8. The method of claim 6, further comprising, under control of one or more processors of the ablation power generator configured with specific executable instructions, generating an alert when the level detector indicates the REA is in the disengaged state.

9. The method of claim 6, further comprising, under control of one or more processors of the ablation power generator configured with specific executable instructions, testing and selecting a return electrode pair of a plurality of return electrode pairs within the REA based on the indicator generated by the level detector.

* * * * *

UNITED STATES PATENT AND TRADEMARK OFFICE
CERTIFICATE OF CORRECTION

| | |
|---|---|
| PATENT NO. | : 12,144,534 B2 |
| APPLICATION NO. | : 16/446458 |
| DATED | : November 19, 2024 |
| INVENTOR(S) | : William Winstrom |

Page 1 of 1

It is certified that error appears in the above-identified patent and that said Letters Patent is hereby corrected as shown below:

In the Specification

At Column 1, Line number 38, delete "circuit," and replace with --circuit.--.
At Column 1, Line number 51, delete "6 Celsius" and replace with --6° Celsius--.
At Column 4, Line number 16, delete "in" and replace with --In--.
At Column 5, Line number 5, delete "rise, at" and replace with --rise at--.
At Column 7, Line number 6, delete "right lea" and replace with --right leg--.
At Column 8, Line number 8, delete "2000Ω" and replace with --200Ω--.
At Column 8, Line number 13, delete "2000Ω" and replace with --200Ω--.
At Column 9, Line number 35, delete "(I=0)" and replace with --(I≈0)--.
At Column 9, Line number 44, delete "osculation" and replace with --oscillation--.
At Column 10, Line number 12, delete "(Z) 244" and replace with --(Z') 244--.
At Column 10, Line number 20, delete "(Z) 244" and replace with --(Z') 244--.
At Column 10, Line number 35, delete "212, hi" and replace with --212. In--.
At Column 11, Line number 21, delete "bop" and replace with --loop--.
At Column 11, Line number 27, delete "wet" and replace with --$v_{ref}$--.
At Column 13, Line number 67, delete "bop" and replace with --loop--.
At Column 14, Line number 57, delete "failing" and replace with --falling--.
At Column 15, Line number 42, delete "&de" and replace with --side--.
At Column 15, Line number 54, delete "fails" and replace with --falls--.
At Column 16, Line number 3, delete "11$" and replace with --118--.

Signed and Sealed this
Seventh Day of January, 2025

Derrick Brent
*Acting Director of the United States Patent and Trademark Office*